United States Patent

Pandey et al.

[11] 4,065,384
[45] Dec. 27, 1977

[54] GRAFT THIN LAYER CHROMATOGRAPHY

[75] Inventors: Ramesh C. Pandey, Champaign; Kenneth L. Rinehart, Jr., Urbana, both of Ill.

[73] Assignee: University of Illinois Foundation, Urbana, Ill.

[21] Appl. No.: 735,759

[22] Filed: Oct. 26, 1976

[51] Int. Cl.² ............................................. B01D 15/08
[52] U.S. Cl. .............................. 210/31 C; 210/198 C
[58] Field of Search ......................... 210/31 C, 198 C

[56] References Cited

U.S. PATENT DOCUMENTS

| | | | |
|---|---|---|---|
| 3,585,129 | 6/1975 | Delfel | 210/198 C |
| 3,623,602 | 11/1971 | Valente | 210/198 C |
| 3,623,841 | 11/1971 | Kraffczyk et al. | 210/31 C |
| 3,864,250 | 2/1975 | Perry | 210/198 C |

Primary Examiner—John Adee
Attorney, Agent, or Firm—Mathew L. Kalinowski

[57] ABSTRACT

A novel plate system for thin layer chromatography comprises a supporting plate coated over about 50-90% of its area with an adsorbent layer, the uncoated surface comprising at least one strip of uniform width along an end of the supporting plate. Two such plates grafted and clamped in a lap-joint so that the edges of the adsorbent layers are in intimate contact provide an assembly on which a chromatogram developed on the first plate can be transferred in whole or in part onto the second plate. The assembly and technique are particularly useful for preparative thin layer chromatography.

16 Claims, 6 Drawing Figures

GRAFT THIN LAYER CHROMATOGRAPHY

The invention described herein was made in the course of work under grant from the Department of Health, Education, and Welfare.

This invention relates to a novel plate system for thin layer chromatography (TLC). In a specific embodiment this invention relates to a novel multi-plate system and method for TLC that provides for transferring of a chromatogram in whole or in part from one plate to another grafted to it. The TLC system together with the grafting technique can be utilized advantageously in analytical or preparative TLC.

Thin layer chromatography employs a moving phase which is usually a solvent or a mixture of solvents and a stationary phase which is usually an adsorbent coated in a thin layer upon a flat supporting surface such as a glass plate. The mixture of compounds to be separated by TLC is dissolved in a solvent and is applied as a spot on the adsorbent layer near one end of the plate. For preparative TLC the solution is applied in a thin band across and near one end of the plate. The plate is then placed in a developing chamber containing solvent in the bottom in a manner such that the solvent wets the adsorbent layer on the end nearest the applied sample spot or band. The chamber is then closed and the solvent ascends the adsorbent layer by capillary action. The development is permitted to proceed until the original spot is resolved into a series of spots or until the original band is resolved into a series of bands. If the spots or bands of the chromatogram developed in this manner are not colored they can be visualized by iodine vapors, ultraviolet light, sulfuric acid spray, or other known methods.

A series of spots separated in a chromatogram can be further resolved by employing two-dimensional TLC. In this technique, the plate containing the series of spots is removed from the developing chamber, dried, rotated 90° and replaced in the developing chamber in a second solvent so that the spots separated during the first development are at the bottom and are again chromatographed. The second solvent may be the same as or different from the first solvent.

A series of bands in a chromatogram can be utilized in preparative TLC. The bands can be scraped off the plate and each band can be eluted from the adsorbent with a polar solvent. Upon removal of solvent, components of the original mixture are obtained which if high resolution and purity are required can be chromatographed again on another plate.

For both two-dimensional analytical TLC and preparative TLC the procedures involve several steps and are time consuming. In the case of preparative TLC, the adsorbent containing the compound to be isolated must be scraped from one plate, eluted with solvent, and then reapplied and redeveloped on another plate.

The above-mentioned and other disadvantages of conventional TLC can be overcome by utilizing the TLC plate system of this invention which comprises a rectangular supporting plate and an adsorbent layer thereon coating about 50–90% of the surface of the supporting plate, the uncoated surface comprising at least one strip of uniform width along an end of the supporting plate. In use, two such plates are joined in a lap-joint which is formed when the uncoated end of one plate laps the adsorbent layer of the second plate in a manner such that the edges of the adsorbent layers of the two plates are in intimate contact along the line of joining. It is important that the joining edges of the adsorbent layers are accurately shaped so that such intimate contact can be established. Clamping means are used at the lap-joint to provide a rigid and stable assembly. With the above-described TLC plate system, the bands of the chromatogram developed in preparative TLC on the first plate can be transferred, in whole or in part, onto the adjoining plate. If desired, the same band can be transferred from two or more plates to a single graft plate. In addition, intermediate bands can be transferred to separate plates one after the other. In the case of analytical TLC, separate samples spotted and developed on the first plate can be transferred to narrow individual plates attached above each ascending chromatogram. For some applications, different adsorbents in adjacent plates can be employed advantageously. These and other advantages of the plate system of this invention are further illustrated by reference to the drawings and description of the preferred embodiments.

FIGS. 1a, 1b, and 1c illustrate the partially coated plates of this invention.

Conventionally, the plate system for TLC generally comprises supporting plates of glass, plastic, or metal in three standard sizes: 5 × 20 cm, 10 × 20 cm, and 20 × 20 cm. A uniform adsorbent layer, 0.1 - 2 mm in thickness, is cast upon the supporting plate from aqueous slurry, and is then dried and activated by heat. The dimensions of the plates and the thickness of the adsorbent layer are not critical. Widely used adsorbents are silica gel, alumina, kieselguhr, and cellulose, which may be used alone or in mixtures. The preparation of conventional plate systems is well known and is facilitated through the use of a variety of commercial equipment available for casting uniform adsorbent layers onto support plates. In addition, ready-made stationary phases of almost any combination of adsorbent and supporting surfaces are available from commercial sources.

Figure 1A:
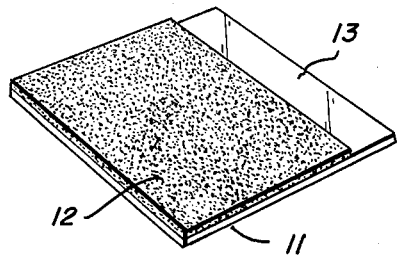

An example of the TLC plate system of this invention was prepared by clamping a 4 × 20 glass plate on a 20 × 20 cm plate to keep the overlapped area uncoated with adsorbent. Suitable adsorbents are well known and readily available from commercial supply houses. A preferred adsorbent is silica gel containing a small amount of calcium sulfate binder which was slurried with water in a proportion of about 30 parts adsorbent to about 60–65 parts water. The slurry was cast upon the glass plate to provide an adsorbent layer ranging in thickness from about 0.1 mm to about 2 mm, preferably about 1 mm. The cast film was allowed to stand for about 30 to 60 minutes and was then activated by heating at about 110° C for about 1 hour. The finished plate is illustrated in FIG. 1a wherein the glass plate 11 is coated with adsorbent layer 12; uncoated area 13 provides means for forming a lap-joint with the second plate of FIG. 1b.

Figure 1B:
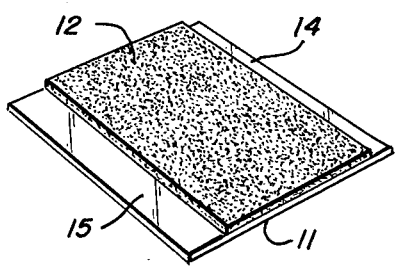

The plate in FIG. 1b is formed in a similar manner on a 20 × 20 cm glass plate by masking a 4 × 20 cm strip 15 at one end and a narrow 1 × 20 cm strip 14 at the opposite end of the plate.

Figure 1C:
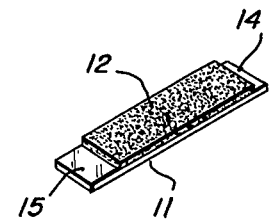

Shown in FIG. 1c is a narrow version of the FIG. 1b plate formed in a similar manner; this narrow plate is conveniently used in analytical TLC.

Figure 2:
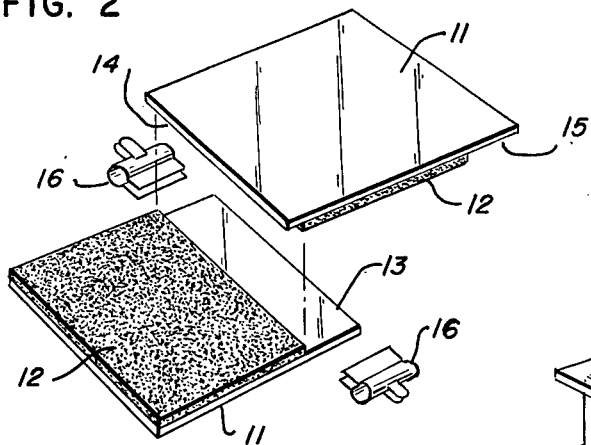
FIG. 2 shows the method of lap-joining two plates to provide for transferring of a chromatogram from one plate to another.
Figure 3:
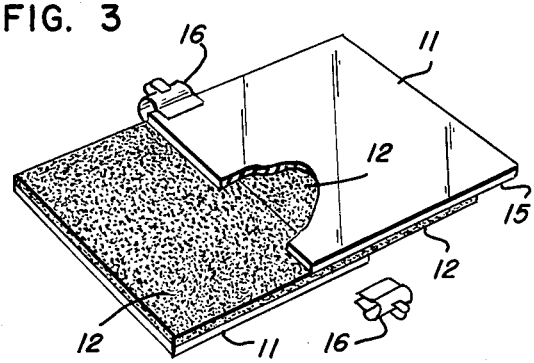
FIG. 3 shows the relative positions of the two plates and adsorbent layers at the lap-joint.

FIG. 2 shows the manner of forming the lap-joint, together with clamping means 16 to form a stable and rigid assembly and to assure that the adsorbent layers are in contact as shown in FIG. 3. It is preferable as shown in FIG. 3 to have the narrow strip 14 of the plate of FIG. 1b lap-joined with strip 13 of the plate of FIG. 1a. The chromatogram transferred at the narrow strip end can then be developed efficiently with a lesser depth of solvent in the developing tank.

Figure 4:
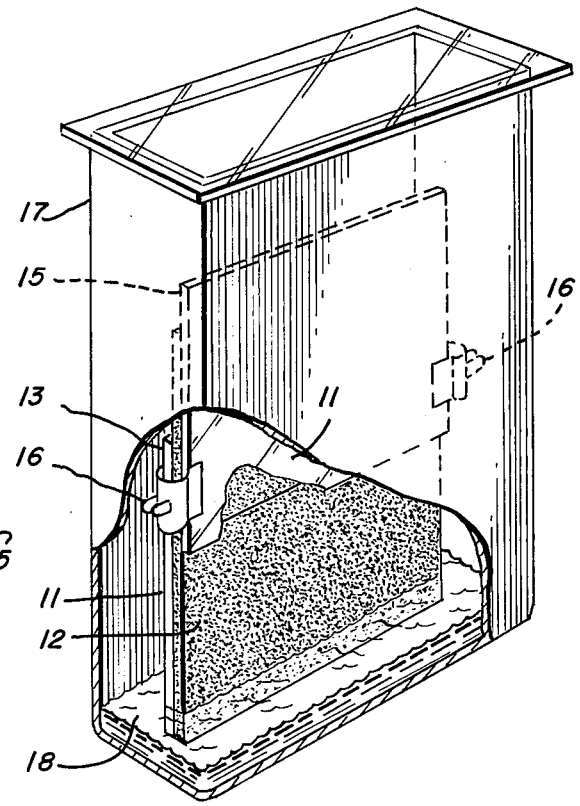
FIG. 4 illustrates the use of the assembled plates of FIG. 3 in a developing tank.

FIG. 4 illustrates the position of the assembly of FIG. 3 in developing tank 17 containing a suitable solvent 18.

In use of the plate system for preparative TLC, the mixture of compounds to be separated is applied in solution in a narrow band to the adsorbent at the end opposite the uncoated end. The assembly is then placed into a developing chamber and the chromatogram is developed with a suitable solvent. Development is continued until the desired band or bands are transferred onto the second plate. The plate with the transferred bands is then detached from the first plate and developed in the same or different solvent in the developing tank. The procedure can be repeated with fresh graft plates as many times as necessary until adequate separation is achieved. The final plate is then dried and the separated bands are worked up in the usual way by scraping the plate or by eluting with an appropriate solvent. With the above-described plate system and technique, purification was effected of mixtures of 2,4-dinitrophenyl hydrazone derivatives of aromatic and aliphatic ketones and aldehydes and derivatives of antibiotics such as geldanomycin.

It is clear that many modifications of the stationary plate system and its uses in graft TLC are possible. For example any convenient size supporting plate can be used; particularly useful are the commercially available rectangular glass plates in 5 × 20 cm, 10 × 20 cm, and 20 × 20 cm sizes. Suitable adsorbents include silica gel, alumina, kieselguhr, and cellulose which may be applied in thicknesses ranging from about 0.5 mm to about 2 mm. For a 20 × 20 cm plate the uncoated strips required for forming the lap-joint can vary from about 1 cm to about 10 cm, i.e. from about 5% to about 50% of the area of the plate.

It is also clear that the present invention offers many advantages over prior-art TLC, among them being 1. "two-dimensional" TLC is possible on a preparative scale;
2. simultaneous spotting and developing of several samples and transfer of each sample to individual plates is possible on an analytical scale;
3. the need is eliminated for scraping the adsorbent containing the desired compound from one plate, eluting with solvent and reapplying to another plate for further purification;
4. transfer of the band(s) from one plate to another is quantitative;
5. the same band can be transferred from two or more plates to a single graft plate and then purified by using a different solvent system;
6. the intermediate bands can be transferred to separate plates one after the other;
7. different adsorbents can be employed in adjacent plates; and
8. "two-dimensional" TLC can be carried out with different adsorbents.

What is claimed is:

1. A TLC plate system for graft thin-layer chromatography comprising a rectangular supporting plate and an adsorbent layer thereon coating about 50% to about 90% of the surface of the supporting plate, the uncoated surface comprising at least one strip of uniform width along an end of the supporting plate and the adsorbent edge adjacent to the uncoated surface being true and square to assure full and intimate contact between adsorbent layers when joined to another of said plate systems in a lap joint.

2. The plate system of claim 1 wherein the adsorbent comprises a uniform layer having a thickness of about 0.1 to about 2 mm and is selected from the group consisting of silica gel, alumina, kieselguhr, and cellulose.

3. The plate system of claim 2 wherein the rectangular supporting plate is about 20 cm in width and ranges from about 5 cm to about 20 cm in length, and is selected from the group consisting of plate glass, plastic sheet, and metal sheet and wherein the uncoated strip ranges in width from about 1 cm to about 10 cm.

4. The plate system of claim 3 wherein the rectangular supporting plate is a 20 × 20 cm glass plate, coated with silica gel to a thickness of about 1 mm over a 20 × 16 cm area, the uncoated area comprising a strip of about 4 cm in width at one end of the glass plate.

5. The plate system of claim 1 wherein the uncoated surface comprises two strips of uniform width along opposite ends of the supporting plate.

6. The plate system of claim 5 wherein the adsorbent comprises a uniform layer having a thickness of about 0.1 to about 2 mm and is selected from the group consisting of silica gel, alumina, kieselguhr, and cellulose.

7. The plate system of claim 6 wherein the rectangular supporting plate is about 20 cm in width and ranges from about 5 cm to about 20 cm in length, and is selected from the group consisting of plate glass, plastic sheet, and metal sheet and wherein one uncoated strip ranges in width from about 1 to about 3 cm and the other uncoated strip ranges in width from about 2 to about 7 cm.

8. The plate system of claim 7 wherein the rectangular supporting plate is a 20 × 20 cm glass plate, coated with silica gel to a thickness of about 1 mm over a 20 × 15 cm area, and wherein one uncoated strip has a width of about 1 cm and the other uncoated strip has a width of about 4 cm.

9. A TLC plate system for graft thin-layer chromatography comprising:
   a. a pair of lap-joined plates each of which plates comprises a rectangular supporting surface and an adsorbent layer thereon coating about 50% to about 90% of the surface of the supporting plate, the uncoated surface comprising at least one strip of uniform width along an end of the supporting plate; and
   b. clamping means for securing the plates at the lap-joint formed when the uncoated strip of the first plate is placed over the adsorbent layer of the second plate in a manner such that the adsorbing layers of the two adjoining plates are in intimate contact along their entire length so as to permit a chromatogram developed initially on the first plate to be transferred, in part or in whole, onto the adsorbent layer of the second plate.

10. The TLC plate system of claim 9 wherein the adsorbent comprises a uniform layer having a thickness of about 0.1 to about 2 mm and is selected from the group consisting of silica gel, alumina, kieselguhr, and cellulose.

11. The TLC plate system of claim 10 wherein the rectangular supporting plates are about 20 cm in width and range from about 5 cm to about 20 cm in length, and are selected from the group consisting of plate glass, plastic sheet, and metal sheet and wherein the uncoated surface of the first plate comprises a single strip ranging in width from about 1 cm to about 10 cm, and the uncoated surface of the second plate comprises two strips at opposite ends of the plate, the first strip ranging in width from about 1 cm to about 3 cm and the second strip ranging in width from about 2 cm to about 7 cm.

12. The TLC plate system of claim 11 wherein the rectangular supporting plates are 20 × 20 cm glass plates coated with silica gel to a thickness of about 1 mm and wherein the uncoated surface of the first plate comprises a single strip about 4 cm in width at one end of the plate, and the uncoated surface of the second plate comprises two strips at opposite ends of the plate, the first strip being about 1 cm in width and the second strip being about 4 cm in width.

13. A method of transferring a chromatogram of a mixture of compounds from a first plate to a second plate each of said plates comprising a rectangular supporting plate and an adsorbent layer thereon coating about 50% to about 90% of the surface of the supporting plate, the uncoated surface comprising at least one strip of uniform width along an end of the supporting plate, which method comprises:
  a. joining and securing the two plates in a lap-joint which is formed when the uncoated strip of the first plate is placed over the adsorbent layer of the second plate in a manner such that the adsorbing layers of the two joining plates are in intimate contact along their entire length;
  b. applying a solution of the mixture of compounds to be chromatogrammed to the adsorbent layer of the first plate; and
  c. developing the chromatogram for a time sufficient to transfer at least a portion of the chromatogram from the first plate to the second plate.

14. The method of claim 13 wherein the adsorbent comprises a uniform layer having a thickness of about 0.1 to about 2 mm and is selected from the group consisting of silica gel, alumina, kieselguhr, and cellulose.

15. The method of claim 14 wherein the rectangular supporting plates are about 20 cm in width and range from about 5 cm to about 20 cm in length, and are selected from the group consisting of plate glass, plastic sheet, and metal sheet and wherein the uncoated surface of the first plate comprises a single strip ranging in width from about 1 cm to about 10 cm, and the uncoated surface of the second plate comprises two strips at opposite ends of the plate, the first strip ranging in width from about 1 to about 3 cm and the second strip ranging in width from about 2 cm to about 7 cm.

16. The method of claim 15 wherein the rectangular supporting plates are 20 × 20 cm glass plates, coated with silica gel to a thickness of about 1 mm and wherein the uncoated surface of the first plate comprises a single strip about 4 cm in width at one end of the plate and the uncoated surface of the second plate comprises two strips at opposite ends of the plate, the first strip being about 1 cm in width and the second strip being about 4 cm in width.

* * * * *